US008249326B2

(12) United States Patent
Macaulay et al.

(10) Patent No.: US 8,249,326 B2
(45) Date of Patent: Aug. 21, 2012

(54) APPARATUS AND METHODS FOR AUTOMATED ASSESSMENT OF TISSUE PATHOLOGY

(75) Inventors: Calum E. Macaulay, Vancouver (CA); Martial Daniel Guillaud, Vancouver (CA); Miriam Pearl Rosin, Port Moody (CA)

(73) Assignee: British Columbia Cancer Agency Branch, Vancouver (CA)

( * ) Notice: Subject to any disclaimer, the term of this patent is extended or adjusted under 35 U.S.C. 154(b) by 1125 days.

(21) Appl. No.: 12/094,974

(22) PCT Filed: Nov. 27, 2006

(86) PCT No.: PCT/CA2006/001933
§ 371 (c)(1),
(2), (4) Date: May 23, 2008

(87) PCT Pub. No.: WO2007/059629
PCT Pub. Date: May 31, 2007

(65) Prior Publication Data
US 2008/0304733 A1    Dec. 11, 2008

Related U.S. Application Data

(60) Provisional application No. 60/739,412, filed on Nov. 25, 2005.

(51) Int. Cl.
*G06K 9/46* (2006.01)
(52) U.S. Cl. .................................................. 382/133
(58) Field of Classification Search .............. 382/128, 382/133
See application file for complete search history.

(56) References Cited

U.S. PATENT DOCUMENTS 6,025,128 A * 2/2000 Veltri et al. ................ 435/6.14
2008/0166035 A1* 7/2008 Qian et al. .................... 382/133

OTHER PUBLICATIONS

Rosin, M.P. et al., "Use of Allelic Loss to Predict Malignant Risk for Low-grade Oral Epithelial Dysplasia", Clinical Cancer Research 2000, 6:357-362.
Garner, D. et al., "The Cyto-Savant System", Automated Cervical Cancer Screening, Igaku-shoin, New York, p. 305-317, 1994.
Doudkine, A. et al., "The comparison of single nucleus analysis and histometric texture feature analysis for detection of MAC in bronchial biopsies", The 8th International Symposium on Diagnostic Quantitative Pathology, Amsterdam, The Netherlands, Sep. 14-16, 1994, p. 171.
Matisic, J.P. et al., "The Use of Nuclear Texture Features for the Analysis of 989 Biopsy-Proven Squamous Atypia", 24th European Congress of Cytology, Ljubljana, Slovenia, Sep. 21-24, 1997.
Guillaud, M. et al., "Nuclear Morphometry as a Biomarker for Bronchial Intraepithelial Neoplasia: Correlation With Genetic Damage and Cancer Development", Cytometry Part A 2005, 63A:34-40.

(Continued)

*Primary Examiner* — Clayton E Laballe
*Assistant Examiner* — Leon W Rhodes, Jr.
(74) *Attorney, Agent, or Firm* — Oyen Wiggs Green & Mutala LLP

(57) ABSTRACT

Methods and apparatus for assessing tissue pathology involve computing an index having a value based upon measures of a plurality of morphological features of cell nuclei in the tissue. The methods may be performed completely automatically or semi-automatically. The index value can be predictive of outcome. The index value may be determined by computing discriminant scores for the cell nuclei based upon values of the measures of morphological features and classifying the nuclei into bins based upon the discriminant score values. The index may be based upon proportions of the nuclei classified in different ones of the bins.

77 Claims, 10 Drawing Sheets

OTHER PUBLICATIONS

Mattie, M. E. et al., "Pathmaster: Content-based Cell Image Retrieval Using Automated Feature Extraction", Journal of the American Medical Informatics Association, vol. 7, No. 4, Jul./Aug. 2000, pp. 404-415.

Poulin, N. et al., "Histometric Texture Analysis of DNA in Thin Sections from Breast Biopsies", Analytical and Quantitative Cytology and Histology, vol. 17, No. 5, Oct. 1995, pp. 291-299.

Henderson et al., "Development of Ganglion Cell Topography in Ferret Retina", The Journal of Neuroscience, Apr. 1988, pp. 1194-1205.

Raimondo, F. et al., "Automated Evaluation of Her—2/neu Status in Breast Tissue From Fluorescent In Situ Hybridization Images", IEEE transactions on Image Processing, vol. 14, No. 9, Sep. 2005, pp. 1288-1299.

Boustany, N. et al. "Calcium-Induced Alterations in Mitochondrial Morphology Quantified in Situ with Optical Scatter Imaging", Biophysical Journal, vol. 83, Sep. 2002, pp. 1691-1700.

International Search Report for PCT/CA2006/001933, International Searching Authority, Apr. 10, 2007.

* cited by examiner

APPARATUS AND METHODS FOR AUTOMATED ASSESSMENT OF TISSUE PATHOLOGY

REFERENCE TO RELATED APPLICATION

This application claims priority from U.S. application No. 60/739,412 filed on 25 Nov. 2005 and entitled NOVEL SYSTEMS AND METHODS FOR ASSESSMENT OF ORAL PRE-MALIGNANT LESIONS. For purposes of the United States of America, this application claims the benefit of the filing date of U.S. patent application No. 60/739,412 filed on 25 Nov. 2005 which is hereby incorporated herein by reference.

TECHNICAL FIELD

This invention relates to apparatus and automated methods for assessing the pathology of tissues. In some embodiments, the invention is applied to evaluating the risk that lesions will develop into cancer.

BACKGROUND

Cancer is a disease that claims a large number of lives each year. For many types of cancer the best currently-known treatments are only partially effective. For example, each year 500,000 people worldwide are diagnosed with head and neck squamous cell carcinoma (HNSC). The 5-year survival rate has remained unchanged at about 50% for the past few decades. For many types of cancer, early detection and treatment are critical to improving the survival rate.

Medical systems around the world lack the financial and other resources to closely follow all patients who have lesions that could be pre-cancerous. A tool capable of evaluating the risk that a lesion will develop into cancer would allow medical resources to be directed in a more focussed manner. For example, the majority (~90%) of oral pre-malignant lesions (OPLs) do not progress to invasive oral squamous cell carcinoma. A method for determining which OPLs will progress to cancer would allow at-risk patients to be followed closely to permit earlier intervention (e.g. surgery, chemoprevention or radiation etc.) with improved survival outcomes. OPLs are pre-neoplastic lesions of the oral cavity. OPLs include conditions described in the field as oral epithelial dysplasia; mild dysplasia; leukoplakia; erythroplakia; hyperplasia; moderate dysplasia; low-grade dysplasia; and, high grade dysplasia.

Current methods for detecting many types of cancer require skilled human intervention. For example, many types of cancer screening are performed by a pathologist or cytotechnologist who examines images of tissue samples for cells that look abnormal to the trained eye.

Standard histopathological grading involves classifying tissues into various categories. for example, OPLs may be classified into the categories "Normal"; "Hyperplasia"; Mild Dysplasia"; "Moderate Dysplasia"; "Severe Dysplasia" and "Squamous Cell Carcinoma". Standard histopathological grading does not correlate well with progression or patient outcome for low-grade lesions and therefore has low prognostic value. Because histological grading involves the application of human judgment, the results are not consistently reproducible. Further, these tissue assessment methods have the disadvantage that they are time consuming and expensive to implement and tend to be qualitative rather than quantitative.

Other techniques for the assessment of tissues (such as loss of heterozygosity ("LOH") measurements, molecular biomarkers, imaging, may provide some prognostic information but are either too slow, costly (or both) to be readily implemented clinically. Further, some such methods can only be performed for lesions that are large enough to provide enough tissue for molecular analysis.

It has been found that LOH patterns can be used to classify OPLs that are not distinguishable by histopathological grading according to cancer risk. Rosin, M. P., et al. *Use of allelic loss to predict malignant risk for low-grade oral epithelial dysplasia*. Clin Cancer Res, 6: 357-362, 2000 used LOH to classify OPLs having minimal (mild/moderate) or no dysplasias into different risk categories. Compared with OPLs without LOH at 3p and 9p (low-risk), those with LOH at 3p and/or 9p but not in other arms (intermediate-risk) demonstrated a 3.8-fold increase in relative cancer risk. OPLs with LOH at 3p and/or 9p plus additional losses (at 4q, 8p, 11q, or 17p, high-risk) demonstrated 33-fold increases in relative cancer risk.

Despite the billions of dollars that have been spent worldwide on cancer research, there is currently, and has been for many years, an urgent need for practical ways to do one or more of:

- detect cancer;
- assess the malignant potential of lesions;
- assess the likely response of a particular cancer to treatment; and,
- assess the disease prognosis (e.g. survival or likelihood of progression to cancer within a time period) of affected patients.

There is a particular need for such ways in relation to oral cancers.

SUMMARY

Various non-limiting embodiments of the invention are described herein. These embodiments are meant to be exemplary and illustrative, not limiting in scope. The various embodiments have different sets of features. As will be apparent to those of skill in the art, features of the example embodiments presented herein may be combined in other combinations and sub-combinations to yield other embodiments of the invention.

Methods and apparatus according to this invention perform quantitative morphometry on the nuclei of cells in tissue from patients.

One aspect of the invention provides methods for the automated assessment of tissue pathology. The methods comprise: obtaining images of a plurality of cell nuclei in a tissue sample; computing values for a plurality of morphometric features of the plurality of cell nuclei, the morphometric features including one or more texture features; from the values of the morphometric features, computing a value for an index characterizing tissue of the tissue sample; and, recording the index value.

Another aspect of the invention provides methods for the automated assessment of tissue pathology. The methods derive an index indicative of a likelihood of an outcome for a tissue. The methods comprise: obtaining images of a plurality of cell nuclei in sample of the tissue; computing values for a plurality of morphometric features of the plurality of cell nuclei; computing discriminant scores for the plurality of nuclei based upon the values of the morphometric features for the nuclei; classifying the nuclei into a bins of a series of bins based upon the discriminant scores for the nuclei; computing the index value based upon the relative numbers of the nuclei classified in the bins; and, recording the index value.

Another aspect of the invention provides methods for the automated assessment of oral lesions. The methods comprise:

obtaining images of cell nuclei in a sample of tissue from the oral lesion; computing values for a plurality of morphometric features of the plurality of cell nuclei; from the values of the morphometric features, computing a value for an index indicative of a likely outcome for the lesion; recording the index value.

Another aspect of the invention provides apparatus for automatically assessing tissue pathology. The apparatus comprises a data processing unit connected to obtain images of cell nuclei in tissue samples. The data processing unit comprises: nucleus identification means for identifying the cell nuclei in the images; feature value computation means for computing values for a plurality of morphometric features of a cell nucleus identified by the nucleus identification means, the morphometric features including one or more texture features; index calculation means for computing a value for an index characterizing the tissue from the values of the morphometric features calculated by the feature value computation means; and, means for recording index values computed by the index calculation means.

Apparatus provided by another aspect of the invention comprises: a data processing unit connected to obtain images of cell nuclei in tissue samples. The data processing unit comprises: nucleus identification means for identifying the cell nuclei in the images; feature value calculation means for computing values for a plurality of morphometric features of the plurality of cell nuclei; discriminant score computation means for computing discriminant scores for the plurality of nuclei based upon the values of the morphometric features for the nuclei; classification means for classifying the nuclei into a bins of a series of bins based upon the discriminant scores for the nuclei; index computation means for computing the index value based upon the relative numbers of the nuclei classified in the bins; and, means for recording the index value.

Another aspect of the invention provides program products comprising media bearing software instructions which, when executed by a data processor, cause the data processor to coordinate the performance of a method according to the invention.

Further aspects of the invention and features of various embodiments of the invention are illustrated in the accompanying drawings and described below.

BRIEF DESCRIPTION OF THE DRAWINGS

Non-limiting exemplary embodiments are illustrated in the drawings.

DESCRIPTION

Throughout the following description specific details are set forth in order to provide a more thorough understanding to persons skilled in the art. However, well known elements may not have been shown or described in detail to avoid unnecessarily obscuring the disclosure. Accordingly, the description and drawings are to be regarded in an illustrative, rather than a restrictive, sense.

Figure 1:
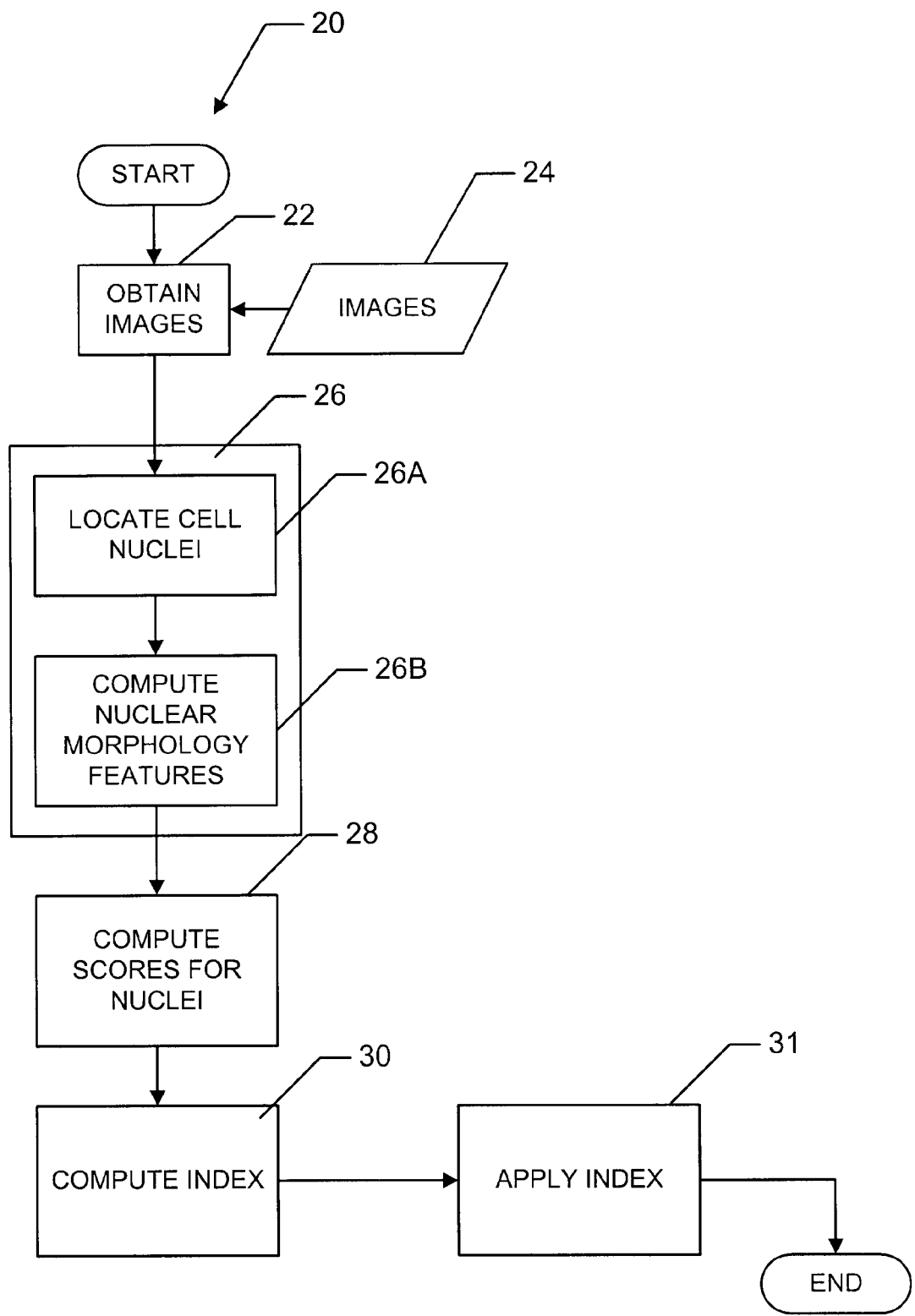
FIG. 1 is a flow chart illustrating a method for assessing the pathology of tissue samples.

FIG. 1 shows a method 20 for determining the malignant potential (risk of progression) of a lesion and the probability of survival of the subject patient. Block 22 obtains images 24 of cells in a tissue sample from the patient. The tissue sample may comprise, for example a biopsy taken from a lesion in the patient. In some embodiments the lesion is an OPL. Images 24 are digital images. Images 24 may be obtained directly from a digital system that images the tissues (such as a digital microphotography system). Images 24 could also be obtained by scanning microphotographs although this adds an additional step.

In a prototype embodiment, images 24 are obtained by imaging thin sections of tissue with a high-resolution imaging system comprising a 12-bit double correlated sampling digital camera designed for interactive analysis of tissue sections. The imaging system is a modified version of the Cyto-Savant automated quantitative system described in Garner, D., et al. *The Cyto-Savant system*, p. 305-317. New York: Igaku-shoin, 1994. The illumination wavelength was 600±5 nm, corresponding to the absorption peak of Thionin stain. The effective pixel sampling space within the plane of the sample was 0.34 $\mu m^2$ and the effective pixel sampling area was 0.116 $\mu m^2$.

Images 24 permit measurement of one or more of the shape, size and texture of DNA distribution within cells in the tissue sample. Various imaging techniques may be used to obtain images 24. Some non-limiting examples of imaging techniques that may be applied to obtain images 24 are:
  optical microscopy of stained tissue specimens;
  phase-contrast microscopy of stained or unstained tissue specimens;
  fluorescence microscopy;
  and the like.
Alternative high-resolution imaging techniques that permit measurement of the morphological features of cell nuclei may also be used to obtain images 24.

In some embodiments the tissue samples are sectioned. This may be performed in any suitable manner. For example, a biopsy, which comprises a full-thickness epithelium in some embodiments, may be prepared by:
  fixing the biopsy in a preservative, such as formalin;
  embedding the biopsy in a suitable material such as paraffin,
  sectioning the embedded biopsy, for example, with a microtome; and,
  where necessary or desirable to enhance the acquisition of images 24, staining the embedded biopsy with a suitable stain. In some embodiments, the stain is a stain that permits the quantitative determination of DNA, for example a Feulgen-Thionin stain. Other stains may be used in other embodiments.
The biopsy may be sectioned along cutting planes extending perpendicular to the surface of the skin in some embodiments.

In some embodiments, the method is carried out in parallel with histopathology grading by a trained person. In such embodiments, some sections of the biopsy may be prepared for histopathology (for example, by staining with a suitable stain such as haematoxylin-eosin) and other sections may be prepared for the acquisition of images 24 by staining with a suitable stain. In some embodiments, a MI is determined from images of haematoxylin/eosin-stained sections (which could be the same sections prepared for histopathological investigation). Such embodiments have the advantages of avoiding the need to make additional sections of the biopsy and eliminating staining steps.

In some embodiments, sample-to-sample variations in staining intensity are corrected for by collecting leukocytes/lymphocytes from the sample. This is optional.

In block 26, image analysis is performed on a number of the cell nuclei that are discernable in images 24. Block 26A locates suitable cell nuclei. In block 26B, the image analysis computes values for each of a plurality of nuclear morphology features of the cell nuclei. Typically the image analysis in block 26 computes the nuclear morphology features for at least 35 cell nuclei. Preferably the image analysis in block 26 computes the nuclear morphology features for 50 or more cell nuclei. In some embodiments, the nuclear morphology features are computed for 50 to 100 cell nuclei.

In some embodiments, the cell nuclei are identified automatically in images 24. In other embodiments, the cell nuclei are selected automatically from intact and in-focus cell nuclei identified in images 24. In some embodiments, the selection of cell nuclei from among the nuclei discernible in images 24 is assisted by a person who may specify by way of a suitable user interface one or more of:
  specific nuclei to be selected;
  regions within an image 24 from within which some or all of the nuclei ought to be selected.

In some embodiments, one or more regions of interest in image 24 may be assisted by location of the corresponding diagnostic area, as determined by a trained pathologist, in an adjacent serial section that has been stained for histopathology.

The nuclear morphology features may include features relating to one or more of:
  the shape of the cell nucleus;
  the size of the cell nucleus; and,
  the texture of DNA distribution within the cell nucleus.

Some examples of shape-related nuclear morphometric features are:
  sphericity;
  harmonics of the nuclear boundary (the Nth harmonic of the nuclear boundary indicates the degree to which the shape of the nuclear boundary can be explained by N lobes;
  other measures of smoothness of the nuclear boundary Some examples of size-related nuclear morphometric features are:
  nucleus area;
  maximum linear dimension of nucleus;

Some examples of texture-related nuclear morphometric features are:
  Density;
  Discrete texture,
  Markovian texture,
  Non-Markovian texture,
  Fractal texture (e.g. fractal area—the relative spatial distributions of high and low optical density variations within the nucleus);
  OD skewedness—a measure of whether the nucleus is dark with light areas or light with dark areas;
  Run-length texture (e.g. long run—a measure of how far across the nucleus one can travel before encountering a significant change in optical density).

In some embodiments, the nuclear morphometric features include at least one or more texture-related features. In some embodiments, the nuclear morphometric features include at least a size-related feature and a texture related feature. In some embodiments, the nuclear morphometric features include at least a shape-related feature and a texture related feature. In a prototype embodiment the values for the features were calculated using Getafics™ tissue section analysis software. Typically the nuclear morphometric features include 4 or more features.

Methods for measuring various nuclear morphological features of cells are known to those of skill in the field automated analysis of images of tissues. For example, some such methods are described in:
  Doudkine, A., et al. *The comparison of single nuclei analysis and histometric texture feature analysis for detection of MAC in breast and bronchial biopsies* Proc. 8th Int'l Symp. on Diagnostic Quantitative Pathology, Amsterdam, The Netherlands, September 14-16, p. 171 (1994);
  Matisic, J. P., et al. *The use of nuclear texture features for the analysis of 989 biopsy proven squamous atypia* 24th European Congress of Cytology, Ljubljana, Slovenia, Sep. 21-24 (1997);
  Poulin, N., al. *Histometric texture analysis of DNA in thin sections from breast biopsies: Application to the detection of malignancy associated changes in carcinoma in situ* Analyt. Quant. Cytol. Histol. 17:291-299 (1995)

In block 28 a score is computed for each cell nucleus based upon the values of the nuclear morphometric features calculated for that nucleus. The score may be computed, for example, by computing a sum or a weighted sum of the values of the nuclear morphometric features for the nucleus.

In block 30 the scores for individual nuclei are combined to yield an index, referred to herein as a morphological index or "MI". The value for the MI is indicative of one or more of:
  the prospects that the lesion will develop into cancer;
  the prospects that cancer of the lesion will recur after treatment;
  the prospects that the patient will survive.

The MI is applied in block 31 by, for example, one or more of:
  displaying the MI to a clinician or other user;
  recording the MI;
  generating a report including the MI;
  comparing the MI to a threshold;
  establishing a prognosis based on the MI;
  scheduling an appointment for treatment or other follow up based on the MI;
  scheduling further tests of the tissue in response to the MI satisfying some criteria;
  etc.

Figure 1A:
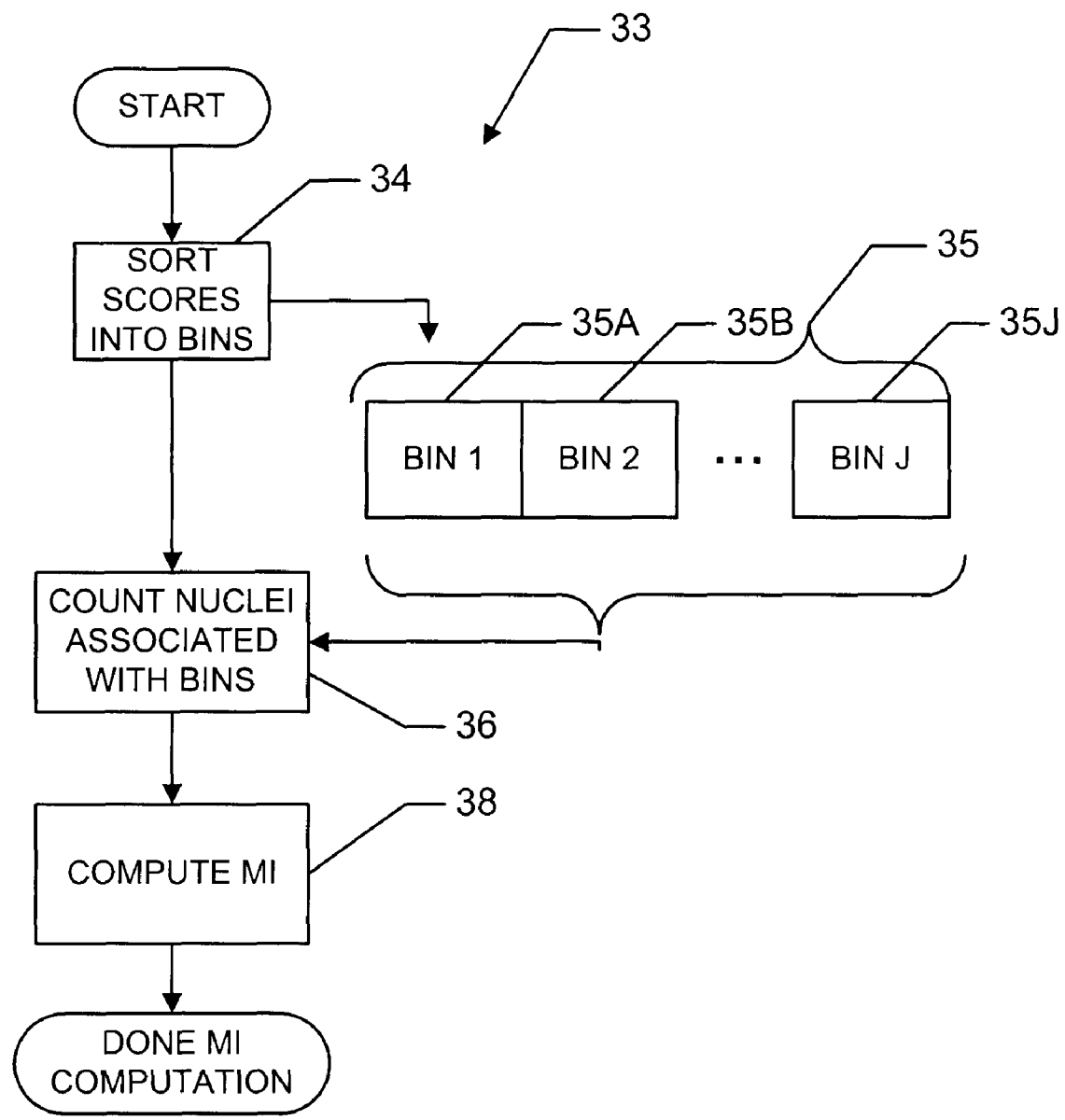
FIG. 1A is a flow chart illustrating a method for computing a morphological index.

In some embodiments, the MI is calculated by a method 33 as shown in FIG. 1A. In block 34 the scores for the different cell nuclei scored in block 28 are sorted into bins 35 according to their scores. In some embodiments there are 4 or more or 5 or more bins. For example, there may be between 4 and 20 bins in some embodiments. In an example embodiment there are 10 bins (identified as 35A to 35J in FIG. 1A).

The number of nuclei that have been associated with each bin 35 is determined in block 36. The MI is computed in block 38. In a preferred embodiment, the MI is computed as a function of the numbers of nuclei having scores falling within the range for each bin. For example, the MI may be computed as a weighted sum of the number of nuclei having scores belonging to each bin (or the percentage of the nuclei having scores in each bin).

Where the score for each nucleus has been computed in such a manner that the score tends to be higher for cancerous (or, more generally, abnormal cells) and the score tends to be lower for normal cells then the higher-valued bins may be weighted significantly more heavily than the lower-valued bins. This tends to produce an MI that discriminates well between normal cells and cells that are cancerous or are disposed to develop cancer.

In a prototype embodiment, the weights used to compute the MI for the 10 bins 35A to 35J are shown in Table 1. It can be observed that the weights increase linearly with bin number in this embodiment. In other embodiments, the weights may increase faster than linearly with bin number.

TABLE 1

Weights for Bins

| Bin | Weight | Bin | Weight |
|-----|--------|-----|--------|
| 35A | 1 | 35F | 6 |
| 35B | 2 | 35G | 7 |
| 35C | 3 | 35H | 8 |
| 35D | 4 | 35I | 9 |
| 35E | 5 | 35J | 10 |

The 10 regions or bins (35A to 35J) represent classes of nuclei with different morphometric characteristics according to their discriminant function scores. For example, bin 35A may cover a range of discriminant score values such that normal-like cells are associated with bin 35A while bin 35J may cover a range of discriminant score values such that cancer-like cells are associated with bin 35J. Bins 35B to 35I cover intermediate ranges of discriminant score. The range of discriminant scores associated with each bin 35 may be set with reference to the scores of nuclei from samples of "normal" tissues and samples of tissues affected by cancer, as described below. The range of discriminant scores for bin 35A may be set so that the scores for normal nuclei tend to fall into bin 35A. The range of scores for bin 35J may be set so that the scores for at least a given percentage of the nuclei from the tissues affected by cancer fall in bin 35J.

In the prototype embodiment, the MI is calculated according to:

$$MI = (1 \times A) + (2 \times B) + (3 \times C) + (4 \times D) + \\ (5 \times E) + (6 \times F) + (7 \times G) + (8 \times H) + (9 \times I) + (10 \times J) \quad (1)$$

where: the letters A through J represent the percentage of nuclei in bins 35A to 35J respectively. An MI calculated according to Equation (1) thus represents the weighted sum of the 10 bins with the numbers (1-10) representing the weight given to the percentage of nuclei in each of the 10 bins. More weight is assigned to the bins associated with nuclei having more cancer-like features. In the prototype embodiment, the MI has possible values in the range of 1 to 10.

Figure 1B:
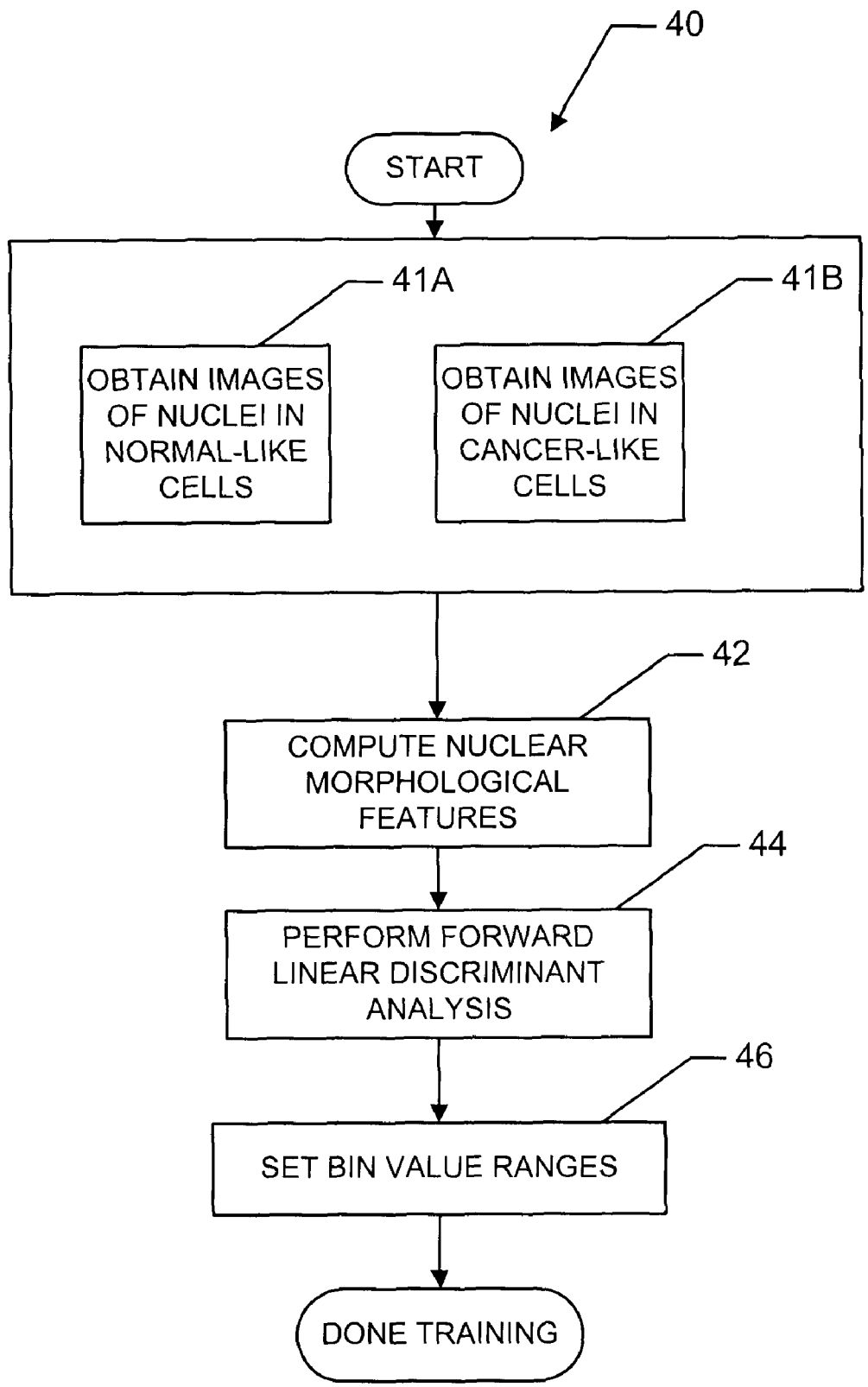
FIG. 1B is a flow chart illustrating a method for training a system that performs the method of FIG. 1.

FIG. 1B illustrates a method 40 that may be used for:
generating the function used in computing the scores in block 28;
selecting nuclear morphological features on which the scores are based; and,
determining the ranges of scores to be allocated to bins 35.

In block 41A images of a number of cell nuclei in normal tissue are obtained. The images may be images of sectioned biopsies obtained as described above, for example. Cell nuclei may be selected from each image as described above. The images of the normal cell nuclei may be described as a "first training set".

In block 41B images of a number of cell nuclei in tissue known to be cancerous are obtained. The images may be images of sectioned biopsies obtained as described above, for example. Cell nuclei may be selected from each image as described above. The images of the normal cell nuclei may be described as a "second training set".

In block 42, the values of each of a set of nuclear morphological features are computed for each of the nuclei in each of the first and second training sets. In a prototype embodiment, the set of nuclear morphological features included 125 different features. The set of features includes one or more texture-based features in some embodiments. The majority of the features are texture-based features in some embodiments. In preferred embodiments, the set of features includes one or more texture-based features, one or more size-based features and one or more shape-based features.

In the prototype embodiment the first training set comprised 5261 cell nuclei selected from 30 biopsies of normal tissue and the second training set comprised 5506 cell nuclei selected from 29 biopsies of tissue known to be affected by oral squamous cell carcinoma.

In block 44 forward linear discriminant analysis is performed to identify a subset of the features that can be used as arguments in a discriminant function that will separate the normal cells from the cancer-like cells. This represents a cell-by-cell classification procedure that assigns a discriminant score to each nucleus (e.g. 50 to 100 nuclei per biopsy) analysed for each OPL biopsy specimen indicating its likely position along the pathway of progression to cancer. Table 2 shows nuclear morphometric features used for forward discriminant analysis in the prototype embodiment.

TABLE 2

Nuclear Morphometric Features Used for Forward Linear Discriminant Analysis for Prototype Embodiment Assessing Oral Preneoplastic Lesions

| Function Name | Coefficient | Description |
|---|---|---|
| Fractal_area 1 | −0.00016 | a measure of the relative spatial distribution of high and low optical density variations in the nucleus—this measure is related to heterochromatin/euchromatin organization |
| OD_Skewness | 0.59 | $3^{rd}$ moment of the nuclear optical density distribution |
| Long90_Run | 0.1484 | run-length features—this provides a measure of chromatin texture |
| Max_radius | −0.1 | maximum radius of the nucleus |
| Harm03_fft | −0.13 | shape—measure of irregularity of the nuclear boundary—in this case the degree to which the boundary can be represented by three lobes. |

The score for a nucleus may be computed by multiplying the value of each nuclear morphometric feature for the nucleus by the corresponding coefficient and then summing the results. For example, the score for the $i^{th}$ nucleus may be expressed as:

$$Score_i = \sum_{j=1}^{j=N} C_j F_{ij} \quad (2)$$

where: $Score_i$ is the score for the $i^{th}$ nucleus; $C_j$ is the coefficient for the $j^{th}$ nuclear morphometric feature; N is the number of nuclear morphometric features; and, $F_{ij}$ is the value for the $j^{th}$ nuclear morphometric feature for the $i^{th}$ nucleus.

In block 46 the ranges of scores to be associated with each bin 35 is determined so that most normal nuclei from the first training set tend to have scores that fall in bin 35A and a desired fraction of nuclei from the second training set have scores that fall into the highest bin (in this prototype case, bin 35J).

Figure 2:
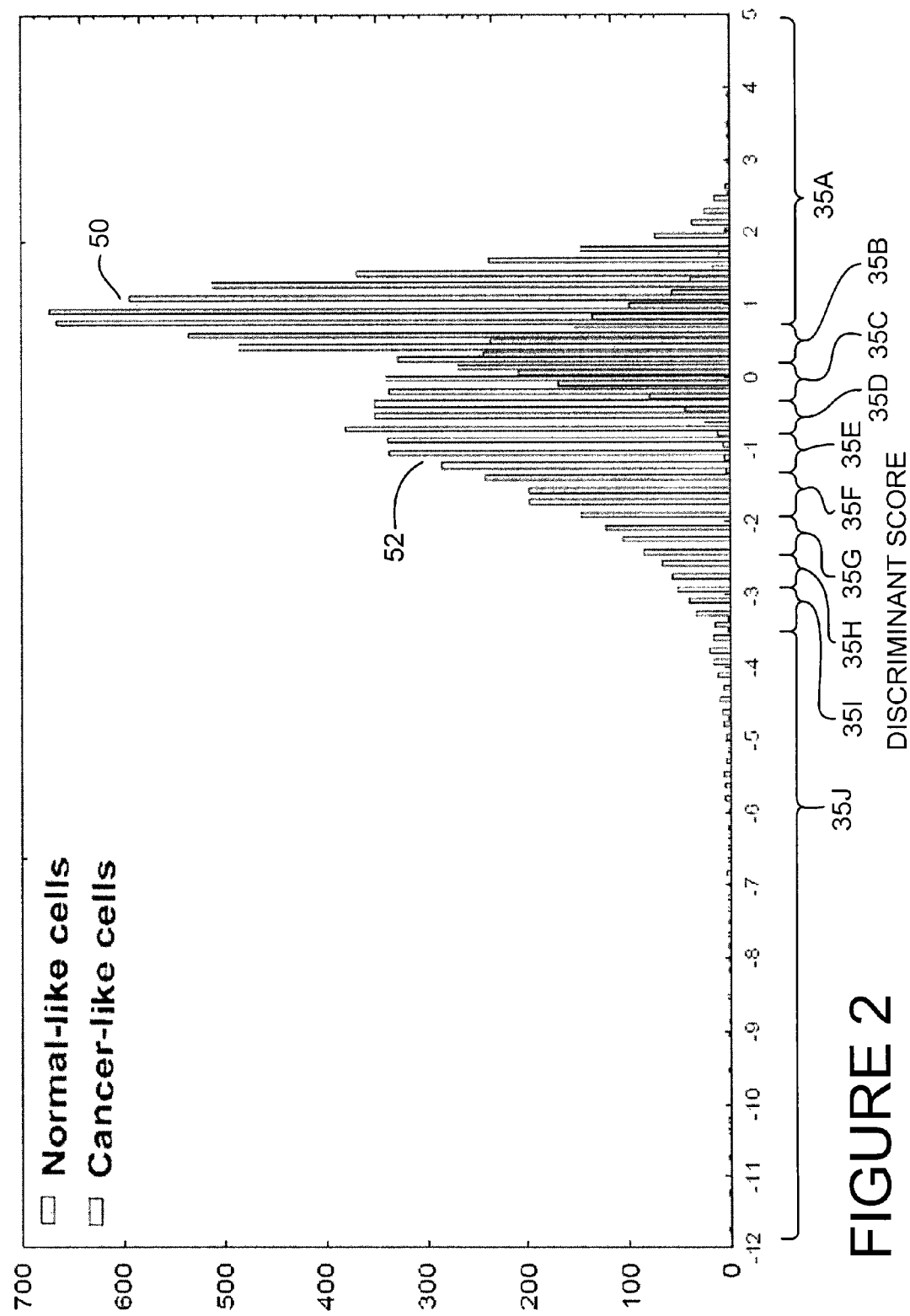
FIG. 2 shows distributions of discriminant scores for normal-like cells and cancer-lice cells.

FIG. 2 shows distributions of the discriminant scores for nuclei in the first training set (identified by reference numeral 50) and the second training set (identified by reference numeral 52). Also shown in FIG. 2 are the discriminant score ranges corresponding to bins 35A to 35J in the prototype embodiment. It can be seen that distribution 50 for the first training set has the form of a normal distribution while distribution 52 for the second training set has a much broader range of discriminant score values (including a significant number of higher discriminant score values) and also has a shape different from that of a normal distribution. The methods described above are sensitive to the different shapes of distributions 50 and 52

One surprising result is that a system can be trained using only normal tissue samples and tissue samples affected by cancer and the system can produce MI values that provide quantitative indications of:
the risk that a lesion will progress to cancer (i.e. the risk of malignant progression);
the overall disease prognosis (survival) of the subject;
the likely response of a lesion to treatment; and/or
the likelihood that cancer will occur after treatment.

An advantage of the embodiment described herein is that the MI may be determined on a lesion-by-lesion basis. This, in turn, can provide one or more of the indications above on a lesion-by-lesion basis. As mentioned above, pathological grading does not itself provide a good indication of the outcome of lesions, especially low-grade lesions such as OPLs. It is not obvious that MI values for different lesions or different patients could have a good correlation to outcomes for those lesions or patients.

A MI determined as described herein may be used on its own or in combination with other diagnostic methods. For example, a MI may be used together with results of: one or more of:
loss of heterozygosity (LOH);
histopathological grading;
toluidine blue staining;
molecular markers; and
various imaging techniques;

to provide a prognosis for a subject. In some embodiments, one or more of the additional diagnostic methods is invoked automatically in response to a MI value exceeding a threshold value.

The value of a MI can be used by a clinician as a basis for determining whether immediate intervention (e.g. local surgery, radiation) is advised or whether watchful waiting is an acceptable alternative to immediate treatment. In some embodiments of the invention, a MI is determined for a patient (or for one or more lesions of a patient). The value of the MI is used as a basis for determining whether to schedule the patient for further tests or treatment. In some embodiments, the MI is automatically compared to a threshold value. Further testing of the patient (or of one or more tissue samples from the patient) or treatment of the patient may be scheduled automatically if the MI reaches or exceeds the threshold value.

In the embodiments described above, a high value for the MI correlates to a greater risk of malignant progression and a reduced long-term survival rate. Conversely, a lower value for the MI correlates to a smaller risk of malignant progression and an increased long-term survival rate.

The prototype embodiment described herein has a number of advantages over current histopathological grading methods performed by skilled humans. Apart from reduced reliance on human resources, which can be important, these advantages include:
Computation of a MI is not subjective;
The MI provides a quantitative measure;
The MI can take into account relationships among different high-risk parameters; and
The MI can be based upon a wider range of tissue phenotypic changes and perform analysis based upon finer details than can a person inspecting an image of a tissue sample visually. For example, an increased chromatin level is known to be a high-risk feature. Traditional pathology judges chromatin level by one criterion, hyperchromatism. By contrast, a MI may be based upon multiple chromatin features or nuclear phenotypes including measures of features such as whether the increased DNA is distributed around the edge of the nucleus or clustered in the centre; whether the nucleus is dark with light areas or light with dark areas and whether the increased chromatin is evenly distributed (euchromatin) or clumped locally (heterochromatin).

In some embodiments, a MI is based upon factors in addition to nuclear morphological features. For example, a MI or the discriminant scores on which the MI is based may be based in part upon one or more of:
cell location (e.g. a layer of tissue in which the cell is found)
cell organization;
in addition to one or more nuclear morphological features.

Figure 3:
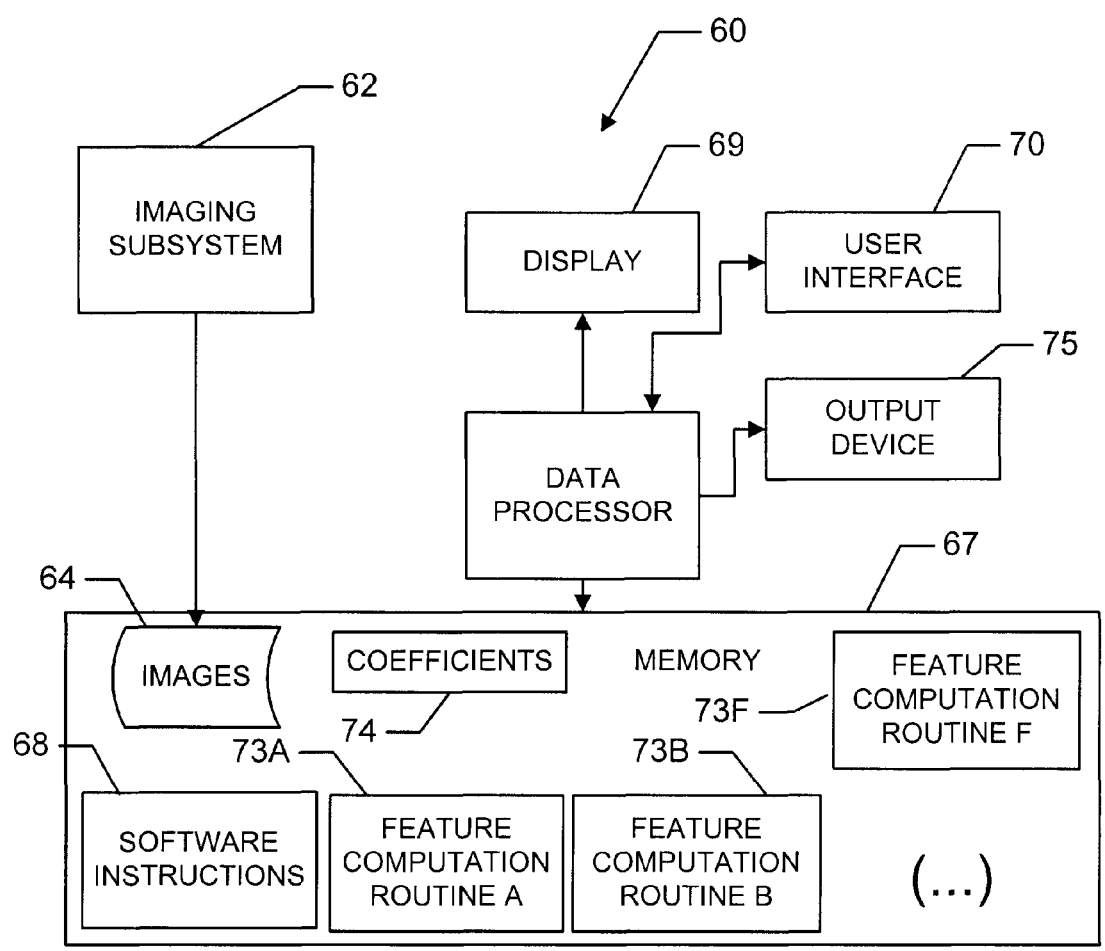
FIG. 3 shows apparatus according to an embodiment of the invention.

FIG. 3 is a block diagram of apparatus 60 according to an embodiment of the invention. Apparatus 60 comprises a high-resolution imaging subsystem 62 that acquires digital images 64. A data processor 66 executes software instructions 68 in a memory 67 accessible to data processor 66. Software instructions 68 cause data processor 66 to identify cell nuclei in images 24. Data processor 66 is connected to a display 69 and a user interface 70. Software instructions 68 optionally cause data processor 66 to display an image 64 on display 69 and to receive input from a human user by way of interface 70 that directs data processor 66 to select certain cell nuclei or cell nuclei from certain areas within image 64.

On each selected cell nucleus, the software instructions cause data processor 66 to compute values for a number of morphology features of the cell nuclei. In the illustrated embodiment, the features are calculated in accordance with software subroutines 73A to 73F in memory 67. The software instructions 68 cause data processor 66 to compute a discriminant score for each cell nucleus based upon a set of stored coefficients 74 and the values computed for the morphological features. Software instructions 68 then cause data processor 66 to compute a MI based upon the discriminant scores.

In some embodiments, processor 66 performs one or more of:
  displaying the MI on display 69;
  printing prints a report that includes the MI on a hard copy output device 75;
  storing the MI in memory 67; and,
  taking a conditional action based upon a value of the MI.
The conditional action may include, for example, one or more of:
  flagging a file for urgent attention;
  generating an electronic message indicating that follow up is required;
  scheduling a patient associated with image 24 (or a tissue sample from the patient) for further tests;
  scheduling an appointment for a patient associated with image 24 for treatment or other follow up; and,
  the like.

Scheduling may be performed by a computer-based scheduling system. The scheduling system may receive input identifying a patient or tissue sample that requires scheduling and may create a job ticket requesting further testing or the like. The scheduling system may maintain records indicating the availability of resources (such as physicians, treatment or diagnostic apparatus, or the like) and schedule the patient for an appointment at a time that a required resource is available. In some embodiments, a priority for an appointment may be based upon a value for the MI such that MI values indicating higher risk of progression to cancer would be allocated appointments with higher priority than for lower MI values.

Image processing and calculation is described above as being performed in a data processor operating under software control. In alternative embodiments of the invention some or all of the image-processing, or computation steps, or both may be performed in specialized image processing or calculating hardware which may include, for example, logic circuits, image processing circuits, suitably-configured field-programmable gate arrays, or the like.

Figure 3A:
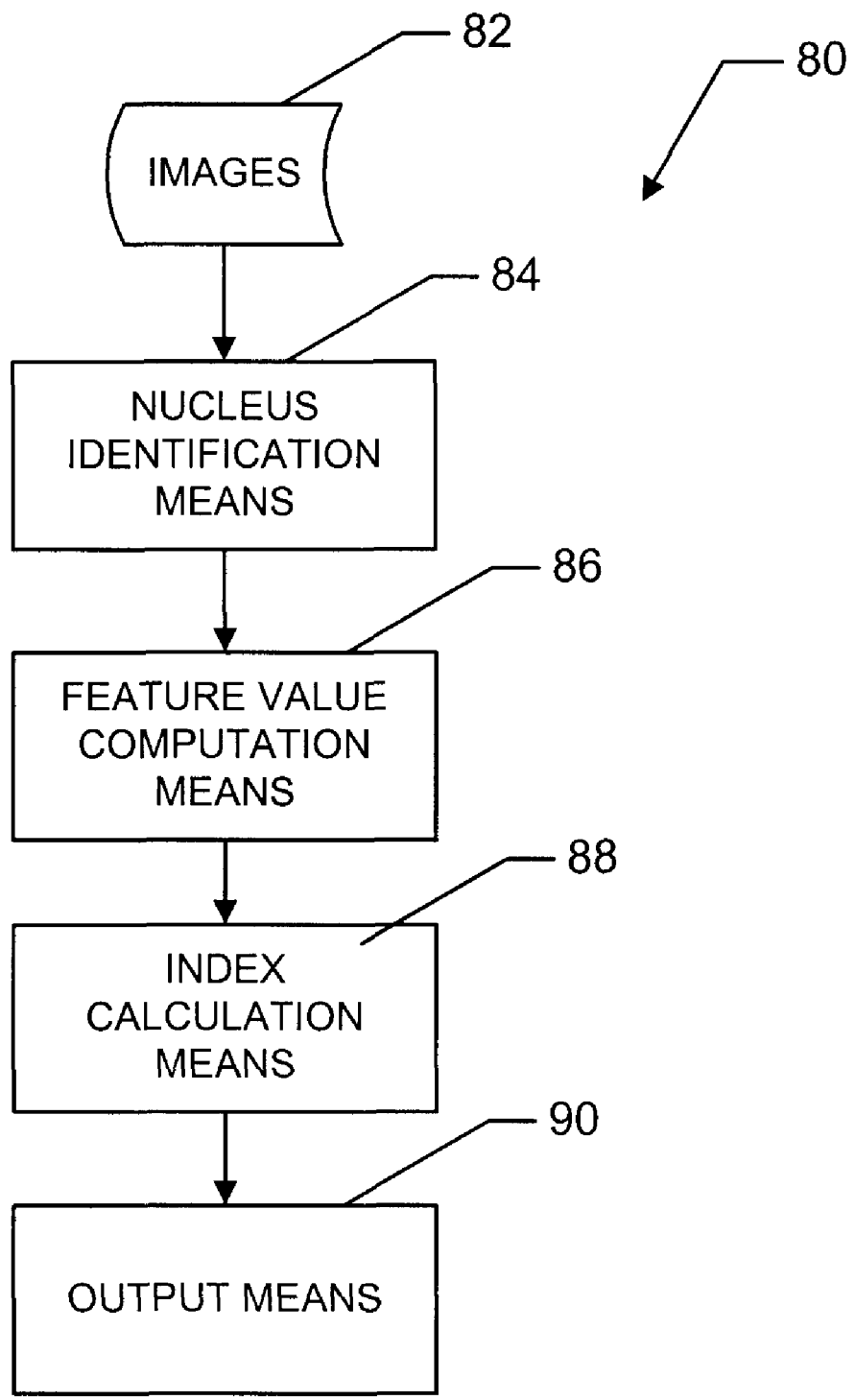
FIG. 3A shows apparatus according to another embodiment of the invention.

FIG. 3A shows apparatus 80 according to another embodiment of the invention. Apparatus 80 acts on images 82. A nucleus identification means 84 identifies cell nuclei in images 82. A feature value computation means 86 computes values for a plurality of morphometric features of a cell nucleus identified by nucleus identification means 84. The morphometric features may include shape features, size features, texture features or mixtures of shape features, size features and texture features. Apparatus 80 has an index calculation means 88 which computes a value for an index characterizing the tissue from the values of the morphometric features calculated by the feature value computation means 86. Apparatus 80 also includes output means 90 for recording, printing, or otherwise exploiting index values computed by the index calculation means 88.

Any of the blocks in FIG. 3A may be implemented in software executing on one or more data processors, in hardware, or in some combination thereof.

EXAMPLE

The inventors have conducted a study in which they have correlated nuclear phenotype changes as measured by an MI determined as described above with: pathological grading, molecular changes and outcome of OPLs. The results of the study showed that the Computer Imaging-detected nuclear phenotype changes correlated strongly with histology grading, genetic damage (LOH) and risk for cancer progression.

MI scores were based upon the nuclear morphometric features and coefficients given in Table 2 for tissue samples from a number of OPLs in a number of patients. 94% of 'normal-like' cells and 77% of the 'cancer-like' cells were correctly classified using these 5 discriminant features. These features were used to generate the cell-by-cell discriminant scores which were amalgamated across all of the cells in each sample to generate the MI for each sample. The samples were divided into a training set, a study set and a test set.

The samples included 83 well-characterized OPLs (a single biopsy per patient) with histological diagnoses of hyperplasia, mild or moderate dysplasia. The lesions were from patients without a prior history of head and neck cancer. Twenty-nine had progressed to cancer and the remaining had not. A prerequisite for inclusion in the study was the availability of an unstained slide that was serial to slides used for previous LOH analysis. Forty-four cases qualified, including 15 progressing (6 hyperplasia, 5 mild dysplasia, and 4 moderate dysplasia) and 29 non-progressing cases (15 hyperplasia, 8 mild dysplasia, and 6 moderate dysplasia). There was no difference between the progressing and the non-progressing lesions in terms of gender, age distribution, and smoking history (all P>0.05). On average, the non-progressing cases had been monitored for over twice the duration of progressing cases (96 months vs. 37 months) to ensure that progression did not occur.

A set of samples from the ends of the phenotypic spectra of oral tissue in neoplastic development were selected as the training set. The training set included 30 oral biopsies (e.g., amalgam tattoo or melanotic macule) with areas of relatively normal oral mucosa and 29 SCCs.

All samples were formalin fixed and paraffin embedded. The histological diagnoses of the samples were reviewed by two oral pathologists. Serial sections, 4-µm in thickness, were cut from each sample and placed on glass slides, one stained with Hematoxylin and Eosin (H & E), and the other with Feulgen-Thionin. Representative areas of the histological diagnosis for each sample were circled on the H & E slide by an oral pathologist, and corresponding areas on the Feulgen-Thionin-stained slide were examined by an automated imaging system.

The MI was correlated with each of: results of histopathological grading (training, study and test sets); molecular pattern (LOH results—for the study set); and outcome (from the study set).

Figure 4:
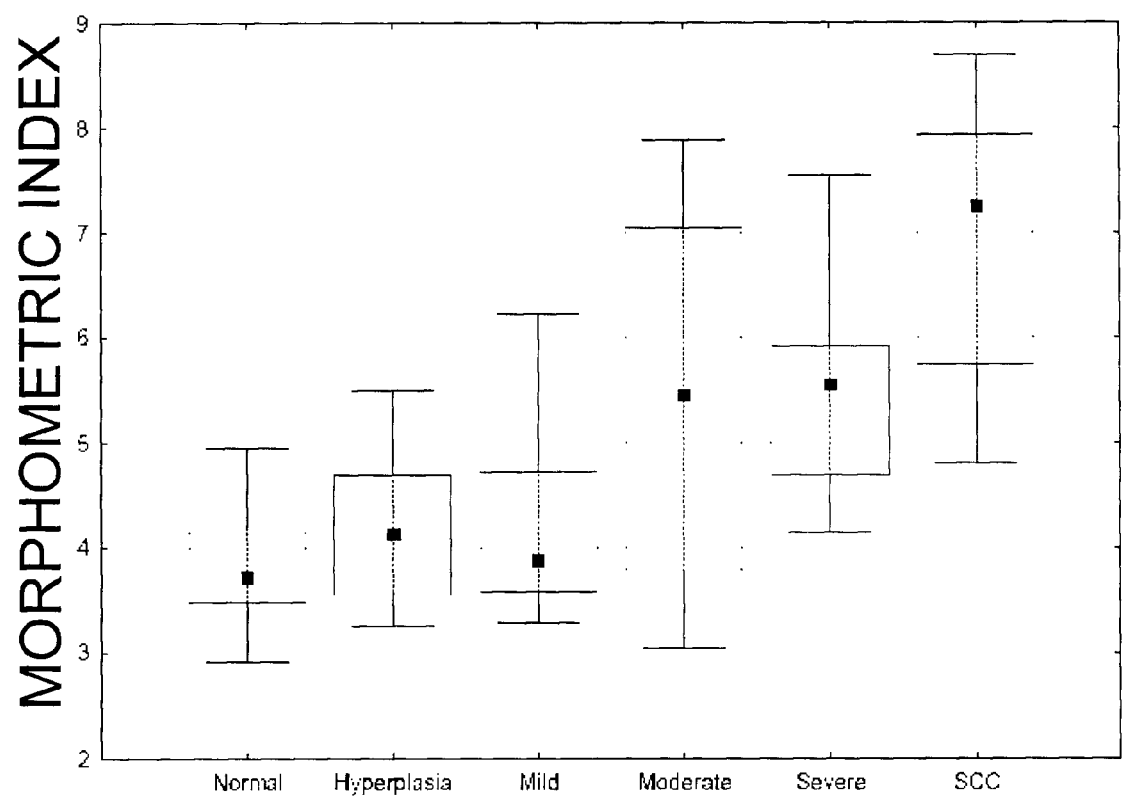
FIGS. 4 and 4A illustrate correlations between morphological index values for a number of oral preneoplastic lesions and histopathological grading for those lesions.
Figure 4A:
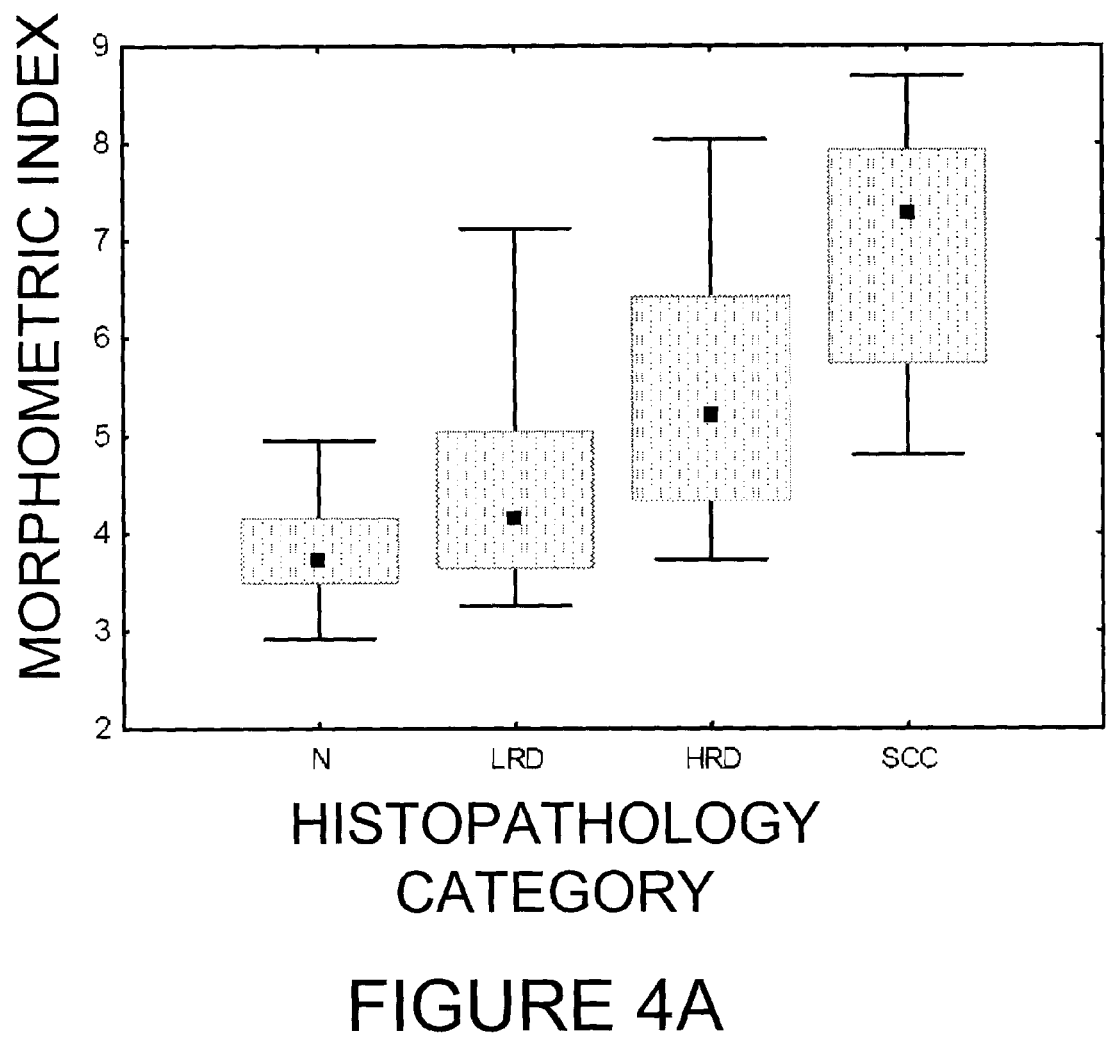

FIGS. 4 and 4A show correlations between the MI and histopathology grade. In FIGS. 4 and 4A, the error bars represent $5^{th}$ and $95^{th}$ percentiles, the boxes represent the central $50^{th}$ percentile the horizontal bar represents the histopathology grade median, and the dark square represents the median of MI values. In FIG. 4A, N stands for "normal"; Hp stands for "hyperplasia"; LG Dys stands for "low-grade dysplasia"; HG Dys stands for "high-grade Dysplasia"; and SCC stands for squamous cell carcinoma".

Table 3 shows association between MI values and molecular risk patterns as evaluated by loss of heterozygosity (LOH) or allelic loss (see Rosin, M. P., et al. *Use of allelic loss to predict malignant risk for low-grade oral epithelial dysplasia*. Clin Cancer Res, 6: 357-362, 2000 for a description of LOH analysis. MI values were consistently higher for samples having LOH at all 7 chromosome regions examined. This increase was significant for 3p (P=0.03), 4q (P=0.002), and 9p (P=0.001). Elevated MI values were strongly associated with the presence of high-risk LOH patterns: multiple losses (P=0.0001), and LOH at 3p &/or 9p plus LOH at any of the arms 4q, 8p, 11q, 13q and 17p (P=0.0001).

TABLE 3

Comparison of MI to LOH Results

|  | With LOH | | Without LOH | | |
| --- | --- | --- | --- | --- | --- |
|  | # of Cases | MI | # of Cases | MI | P-value |
| 3p | 10 | 5.4 ± 1.6 | 28 | 4.3 ± 1.1 | 0.03 |
| 4q | 5 | 6.0 ± 1.3 | 36 | 4.2 ± 1.1 | 0.002 |
| 8p | 8 | 5.1 ± 1.5 | 33 | 4.4 ± 1.2 | 0.18 |
| 9p | 17 | 5.3 ± 1.6 | 26 | 4.0 ± 0.7 | 0.001 |
| 11q | 7 | 5.3 ± 1.7 | 36 | 4.4 ± 1.1 | 0.06 |
| 13q | 3 | 5.0 ± 1.3 | 37 | 4.4 ± 1.12 | 0.38 |
| 17p | 8 | 5.1 ± 1.9 | 35 | 4.4 ± 1.1 | 0.14 |
| Any loss | 23 | 5.0 ± 1.5 | 20 | 3.9 ± 0.5 | 0.004 |
| At least 1 LOH | 15 | 5.5 ± 1.6 | 28 | 4.0 ± 0.7 | 0.0001 |
| At least 2 LOH | 11 | 5.6 ± 1.7 | 32 | 4.2 ± 0.9 | 0.0009 |
| High Risk* | 15 | 5.5 ± 1.6 | 28 | 4.0 ± 0.7 | 0.0001 |

*LOH at 3p and/or 9p plus at least 1 other arm (4q, 8p, 11q, 13q or 17p)

Figure 5:
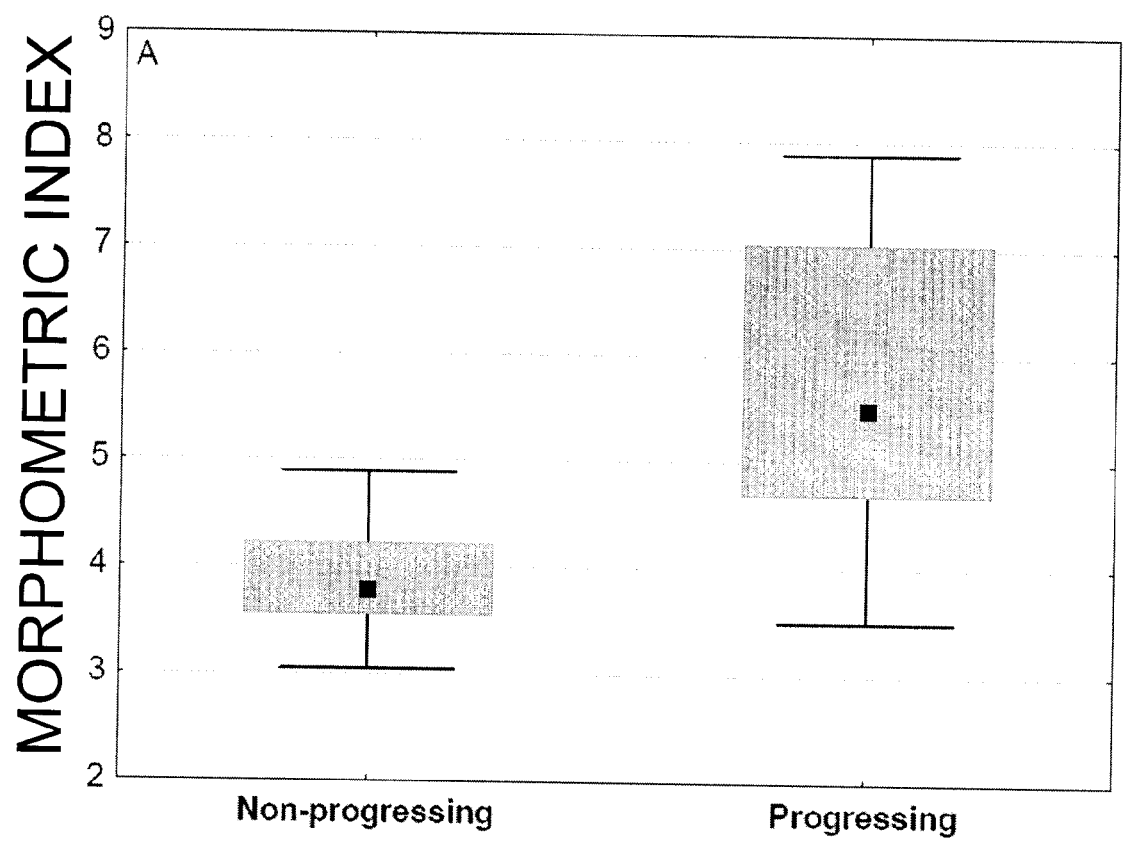
FIG. 5 shows MI values for cases exhibiting hyperplasia and low-grade dysplasia that have been classified according to whether or not they progress to cancer.

FIG. 5 shows MI values for cases exhibiting hyperplasia and low-grade dysplasia that have been classified according to whether or not they progress to cancer. Progressing lesions showed significantly higher MI values than non-progressing lesions (mean MI 5.72±1.36 for progressing lesions vs. 3.94±0.66 for non-progressing lesions; P<0.0001). The difference was still statistically significant even when the hyperplasia and dysplasia were examined separately (smaller sample sets): mean MI 4.74±0.70 for progressing hyperplasia vs. 3.85±0.50 for non-progressing hyperplasia (P=0.004); and mean NPS 6.38±1.31 for progressing low-grade dysplasia vs. 4.03±0.81 for non-progressing low-grade dysplasia (P<0.0001).

These experimental results show that an appropriately-defined MI has values that differ sufficiently depending upon the risk that a lesion will progress to cancer. This makes it possible to create a bright-line test such that lesions having MI below a threshold value can be considered low-risk while lesions having MI values above the threshold value can be considered higher-risk. For the MI used in the prototype embodiment being used to study OPLs, a cutoff value of 4.5 was found to provide good separation between non-progressing lesions and the progressing lesions. In the training set, which consisted of biopsies from lesions graded as either normal or SCC, only 5 of 30 (17%) normal samples had a MI value≧4.5 (high –MI) and 28 of the 29 (97%) of SCC had MI values≧4.5.

When the study set samples (hyperplasia and low-grade dysplasia) were categorized using this threshold value, 17 of the 44 test cases had a high-MI. Molecularly, 16 of these 17 cases exhibited LOH. Of these 16 cases, 11 (69%) showed LOH at 3p &/or 9p, a loss believed to be essential although not sufficient for cancer progression. In contrast, only 7 of the 27 (26%) cases with MI<4.5 (low-MI) showed such a loss (P=0.001).

Prognostically, 13 of the 17 (76%) cases with high-MI progressed to invasive SCC. In contrast, only 2 of the 27 (7%) cases with low-MI progressed to cancer in the study period (P<0.0001). In other words, 86% of non-progressing cases (25/29) and 86% of progressing cases (13/15) were correctly classified by comparing MI values to a threshold.

Time-to-progression curves were plotted as function of the MI classification into one of the two groups (high-MI vs. low-MI). A significant difference was observed between the low-MI group and the high-MI group (P<0.00015). Time to progression was significantly different for these 2 groups. The proportion of lesions progressing to cancer at 5 years was 71% (12/17) for lesions with high-MI and only 22% for lesions with low-MI. There was a 10-fold (RR=10.3 [CI: 2.86-59.8]) increase in the relative risk of progression to cancer for oral lesions with a high-MI in comparison to those with a low-MI.

These results demonstrate the utility of MI values for predicting cancer outcomes (as distinct from grading lesions). The outcomes may comprise, for example, one or more of:
 the risk that a lesion will progress to cancer within some defined period if the lesion is not treated;
 the likelihood that a lesion will not progress to cancer within some defined period;
 the risk that a particular lesion will progress to cancer (or that cancer will recur) after having been treated with a particular treatment or set of treatments; and,
 the likely response of a particular lesion to a specified treatment.

These outcomes may be predicted for low- or higher-grade lesions.

MI values can be used to grade lesions. The MI values tend to increase with increasing severity of histological grading (P<0.0001). MI tends to differ significantly between non-dysplastic lesions and dysplastic lesions; and between dysplastic lesions and invasive cancer. As shown in FIG. 4A, low-grade dysplasia shows the largest variability in MI values among the different histological grades. This indicates that lesions classified as low-grade dysplasia by standard histopathological grading include a mixture of lesions having different potentials for progressing.

Figure 6:
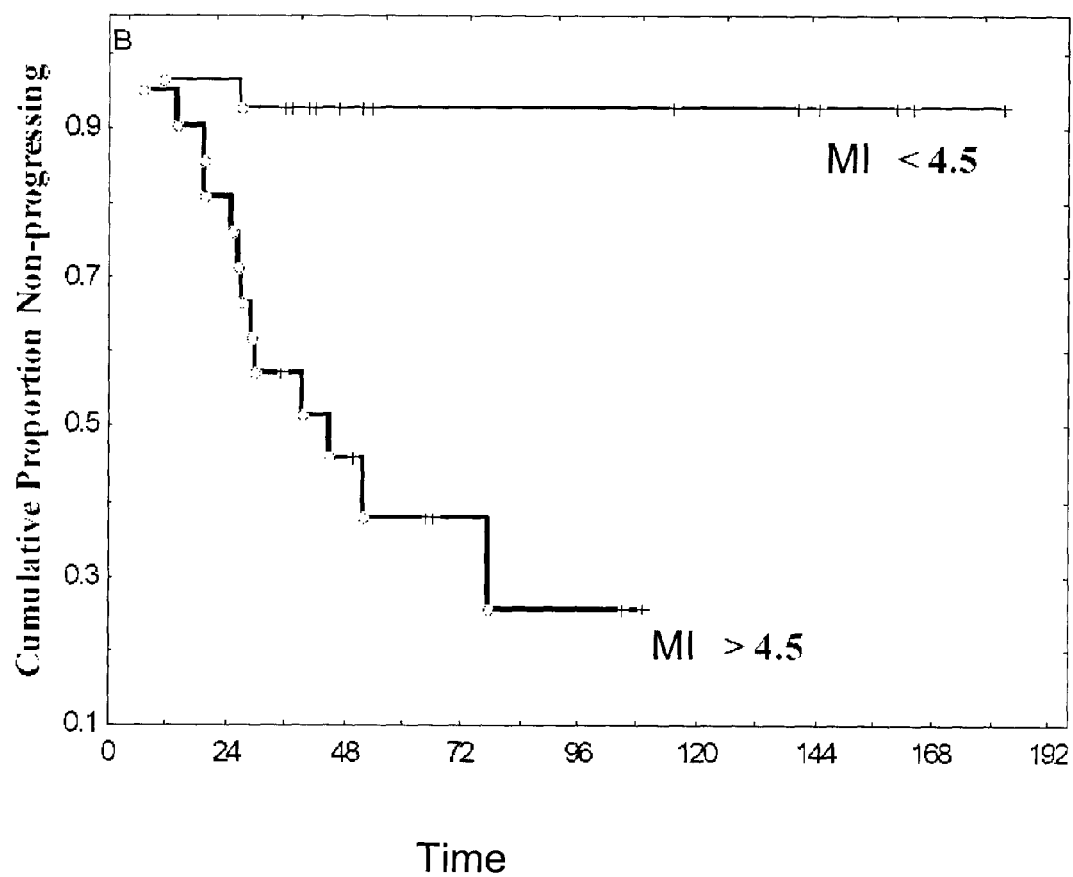
FIG. 6 shows the progression to cancer over time for a set of lesions having morphological index values above a threshold value and another set of lesions having morphological index values below the threshold.

FIG. 6 shows the progression to cancer over time for a set of lesions having morphological index values above a threshold value and another set of lesions having morphological index values below the threshold.

Certain implementations of the invention comprise computer processors which execute software instructions which cause the processors to perform a method of the invention. For example, one or more processors in a computer system may implement the methods of the invention by executing software instructions in a program memory accessible to the processors. The invention may also be provided in the form of a program product. The program product may comprise any medium which carries a set of computer-readable signals comprising instructions which, when executed by a data processor, cause the data processor to execute a method of the invention. Program products according to the invention may be in any of a wide variety of forms. The program product may comprise, for example, media such as magnetic data storage media including floppy diskettes, hard disk drives, optical data storage media including CD ROMs, DVDs, electronic data storage media including ROMs, flash RAM, or the like. The software instructions on the medium may optionally be compressed, encrypted, or both compressed and encrypted.

Where a component (e.g. a software module, processor, assembly, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

While a number of exemplary aspects and embodiments have been discussed above, those of skill in the art will recognize certain modifications, permutations, additions and sub-combinations thereof. By way of non-limiting example:

the specific features used for generating discriminant scores or the functions applied to obtain values for those features may be varied;

the number of features on which the discriminant scores are based may be varied;

the number of nuclei for which features are measured for computation of a MI may be varied;

the number of bins 35 may be varied;

the weighting factors used in computation of the MI may be varied;

individual values for nuclear morphological features or computations of discriminant scores in some embodiments may be performed manually as opposed to by the automated apparatus described above;

alternative functions for computing discriminant scores or for computing the MI from the discriminant scores may be applied;

methods and apparatus according to the invention may be applied to assessing a variety of tissues including oral tissues such as OPLs as described above, bronchial tissues, tissues which can host other epithelial-derived cancers such as the head and neck, cervix, ovary and lung;

It is therefore intended that the following appended claims and claims hereafter introduced are interpreted to include all such modifications, permutations, additions and sub-combinations as are within their true spirit and scope.

What is claimed is:

1. A method for assessing tissue pathology comprising:
   obtaining images of a plurality of cell nuclei in a tissue sample;
   computing values for a plurality of morphometric features of the plurality of cell nuclei, the morphometric features including one or more texture features; and,
   from the values of the morphometric features, computing a value for an index characterizing tissue of the tissue sample; and,
   recording the index value;
   wherein computing the value for the index comprises:
   computing discriminant scores for the plurality of nuclei based upon the values of the morphometric features for the nuclei;
   classifying the nuclei into a bins of a series of bins based upon the discriminant scores for the nuclei; and,
   computing the index value based upon the relative numbers of the nuclei classified in the bins;
   wherein the discriminant scores are based upon at least: a fractal area; a measure of skewedness, and a dimension of the nucleus; and,
   wherein a coefficient associated with the measure of skewedness is opposite in sign to coefficients associated with the fractal area and the dimension of the nucleus.

2. A method for assessing tissue pathology comprising:
   obtaining images of a plurality of cell nuclei in a tissue sample;
   computing values for a plurality of morphometric features of the plurality of cell nuclei, the morphometric features including one or more texture features; and,
   from the values of the morphometric features, computing a value for an index characterizing tissue of the tissue sample; and,
   recording the index value;
   wherein computing the value for the index is performed according to a function having the property that there exists a first range of values for the index for which is a confidence in excess of 50% that the tissue belongs to a progressing phenotype if the index for the tissue is in the first range.

3. A method according to claim 2 wherein computing the value for the index comprises:
   computing discriminant scores for the plurality of nuclei based upon the values of the morphometric features for the nuclei;
   classifying the nuclei into a bins of a series of bins based upon the discriminant scores for the nuclei; and,
   computing the index value based upon the relative numbers of the nuclei classified in the bins.

4. A method according to claim 3 wherein computing the index value based upon the relative numbers of the nuclei classified in the bins comprises computing a weighted sum of the fraction of the nuclei classified in each of the bins.

5. A method according to claim 4 wherein computing the weighted sum comprises multiplying the fraction of the nuclei classified in each of the bins by a weighting coefficient associated with the bin wherein the weighting coefficients increase linearly with bin number.

6. A method according to claim 3 wherein classifying the nuclei comprises sorting the nuclei into at least 5 bins.

7. A method according to claim 6 comprising associating a range of values for the discriminant score with a first one of the bins that corresponds to nuclei of normal-like cells.

8. A method according to claim 7 comprising computing the discriminant scores according to a discriminant function obtained by performing discriminant analysis on a first training set comprising normal-like cells and a second training set comprising cancer-like cells.

9. A method according to claim 7 comprising associating a range of values for the discriminant score with a last one of the bins that corresponds to nuclei of cancer-like cells.

10. A method according to claim 3 wherein the texture features comprise a fractal area.

11. A method according to claim 3 wherein the texture features comprise a measure of a how far across the nucleus one can travel before encountering a significant change in optical density.

12. A method according to claim 3 wherein the texture-related features comprise one or more features selected from the group consisting of: density; discrete texture; Markovian texture; non-Markovian texture; fractal texture; OD skewedness; and, run-length texture.

13. A method according to claim 3 wherein the morphometric features include one or more features having values that measure sizes of the nuclei.

14. A method according to claim 13 wherein the one or more features having values that measure sizes of the nuclei include a feature having a value representing a maximum diameter of the nuclei.

15. A method according to claim 3 wherein the morphometric features include one or more features having values that measure shapes of boundaries of the nuclei.

16. A method according to claim 3 wherein obtaining the images comprises imaging thin sections of tissue with a digital microscope imaging system.

17. A method according to claim 16 wherein the thin sections are stained with a stain.

18. A method according to claim 17 wherein the stain is quantitative for DNA.

19. A method according to claim 18 wherein the stain comprises a Feulgen-Thionin stain.

20. A method according to claim 17 wherein the stain comprises a haematoxylin/eosin stain.

21. A method according to claim 3 wherein the discriminant scores are based upon at least: a fractal area; a measure of skewedness, and a dimension of the nucleus.

22. A method according to claim 3 wherein computing the value for the index is based upon the values for the morphometric features for at least 35 nuclei.

23. A method according to claim 2 comprising comparing the index to a threshold.

24. A method according to claim 23 comprising automatically scheduling a further test on the tissue based upon a result of the comparison.

25. A method according to claim 23 comprising automatically scheduling an appointment for a patient corresponding to the tissue based upon a result of the comparison.

26. A method according to claim 25 wherein automatically scheduling the appointment comprises setting a priority for the appointment according to a value of the index.

27. A method according to claim 2 wherein computing the value for the index is performed according to a function having the property that there exists a second range of values for the index that is non-overlapping with the first range for which there is a confidence in excess of 50% that the tissue belongs to a non-progressing phenotype if the index for the tissue is in the second range.

28. A method according to claim 2 comprising expressing a likelihood of an outcome based upon the value of the index.

29. A method according to claim 28 wherein the outcome comprises a risk of progression to cancer.

30. A method according to claim 28 wherein the outcome comprises a likelihood of recurrence of cancer after a specified treatment.

31. A method according to claim 28 wherein the outcome comprises a likely response of a lesion to a specified treatment.

32. A method according to claim 28 wherein the outcome comprises a prognosis for a lesion.

33. A method according to claim 2 wherein the tissue sample comprises a sample of tissue of an oral lesion.

34. A method according to claim 33 wherein the oral lesion comprises an oral preneoplastic lesion.

35. A method according to claim 33 wherein the oral lesion comprises a low-grade oral lesion.

36. A method according to claim 33 wherein the oral lesion comprises a high-grade oral lesion.

37. A method according to claim 2 wherein the tissue sample comprises a sample of a tissue of a patient's head, neck, lung, cervix, or ovary.

38. A method according to claim 2 comprising computing the value for the index for a plurality of tissue samples corresponding respectively to a plurality of lesions of a patient and automatically prioritizing treatments of the plurality of lesions based upon the index values.

39. A method for assessing tissue pathology comprising:
obtaining images of a plurality of cell nuclei in a tissue sample;
computing values for a plurality of morphometric features of the plurality of cell nuclei, the morphometric features including one or more texture features; and,
from the values of the morphometric features, computing a value for an index characterizing tissue of the tissue sample; and,
recording the index value;
wherein computing the value for the index is performed according to a function having the property that there exists a range of values for the index for which there is a confidence in excess of 50% that the tissue belongs to a non-progressing phenotype if the index for the tissue is in the range.

40. A method according to claim 39 comprising automatically taking a conditional action based upon a value of the index.

41. A method according to claim 40 wherein the conditional action comprises automatically flagging a file for urgent attention.

42. A method according to claim 40 wherein the conditional action comprises automatically ordering further tests on the sample of tissue.

43. A method according to claim 40 wherein the conditional action comprises automatically generating an electronic message indicating that follow up is required.

44. A method according to claim 40 wherein the conditional action comprises automatically scheduling an appointment for a patient associated with the tissue sample.

45. A method according to claim 44 wherein scheduling the appointment comprises automatically setting a priority for the appointment based upon the value of the index.

46. A method according to claim 39 comprising automatically associating an outcome with the index value wherein the outcome comprises a risk of progression to cancer.

47. A method according to claim 46 wherein the outcome comprises a likelihood of recurrence of cancer after a specified treatment.

48. A method according to claim 46 wherein the outcome comprises a likely response of a lesion to a specified treatment.

49. A method according to claim 46 wherein the outcome comprises a prognosis for a lesion.

50. A method for deriving an index indicative of a likelihood of an outcome for a tissue, the method comprising:
obtaining images of a plurality of cell nuclei in sample of the tissue;
computing values for a plurality of morphometric features of the plurality of cell nuclei;
computing discriminant scores for the plurality of nuclei based upon the values of the morphometric features for the nuclei;
classifying the nuclei into a bins of a series of bins based upon the discriminant scores for the nuclei;
computing the index value based upon the relative numbers of the nuclei classified in the bins; and,
recording the index value;
wherein the discriminant scores are based upon at least: a fractal area; a measure of skewedness, and a dimension of the nucleus; and,
wherein a coefficient associated with the measure of skewedness is opposite in sign to coefficients associated with the fractal area and the dimension of the nucleus.

51. A method according to claim 50 wherein computing the index value based upon the relative numbers of the nuclei classified in the bins comprises computing a weighted sum of the fraction of the nuclei classified in each of the bins.

52. A method according to claim 51 wherein computing the weighted sum comprises multiplying the fraction of the nuclei classified in each of the bins by a weighting coefficient associated with the bin wherein the weighting coefficients increase linearly with bin number.

53. A method according to claim 50 wherein classifying the nuclei comprises sorting the nuclei into at least five bins.

54. A method according to claim 53 comprising associating a range of values for the discriminant score with a first one of the bins that corresponds to nuclei of normal-like cells.

55. A method according to claim 54 comprising associating a range of values for the discriminant score with a last one of the bins that corresponds to nuclei of cancer-like cells.

56. A method according to claim 50 comprising comparing the index to a threshold.

57. A method according to claim 56 comprising automatically scheduling a further test on the tissue based upon a result of the comparison.

58. A method according to claim 56 comprising automatically scheduling an appointment for a patient corresponding to the tissue based upon a result of the comparison.

59. A method according to claim 50 wherein obtaining the images comprises imaging thin sections of tissue with a digital microscope imaging system.

60. A method according to claim 59 wherein the thin sections are stained with a stain that is quantitative for DNA.

61. A method according to claim 60 wherein the stain comprises a Feulgen-Thionin stain.

62. A method according to claim 50 comprising automatically taking a conditional action based upon a value of the index.

63. A method according to claim 62 wherein the conditional action comprises automatically flagging a file for urgent attention.

64. A method according to claim 62 wherein the conditional action comprises automatically ordering further tests on the sample of tissue.

65. A method according to claim 62 wherein the conditional action comprises automatically generating an electronic message indicating that follow up is required.

66. A method according to claim 62 wherein the conditional action comprises automatically scheduling an appointment for a patient associated with the tissue sample.

67. A method according to claim 66 wherein scheduling the appointment comprises automatically setting a priority for the appointment based upon the value of the index.

68. A method according to claim 50 comprising computing the discriminant scores according to a discriminant function obtained by performing discriminant analysis on a first training set comprising normal-like cells and a second training set comprising cancer-like cells.

69. A method according to claim 50 comprising automatically associating an outcome with the value of the index.

70. A method according claim 69 wherein the outcome comprises a risk of progression to cancer.

71. A method according to claim 69 wherein the outcome comprises a likelihood of recurrence of cancer after a specified treatment.

72. A method according to claim 69 wherein the outcome comprises a likely response of a lesion to a specified treatment.

73. A method according to claim 69 wherein the outcome comprises a prognosis for a lesion.

74. A method according to claim 50 comprising computing the value for the index for a plurality of tissue samples corresponding respectively to a plurality of lesions of a patient and automatically prioritizing treatments of the plurality of lesions based upon the index values.

75. A method according to claim 74 wherein the plurality of lesions comprise oral lesions.

76. A method according to claim 75 wherein the oral lesions comprise oral preneoplastic lesions.

77. A method according to claim 75 wherein the lesions comprise low-grade lesions.

* * * * *